US00PP31828P2

(12) United States Plant Patent
Mathey

(10) Patent No.: US PP31,828 P2
(45) Date of Patent: Jun. 2, 2020

(54) POMEGRANATE PLANT NAMED 'SMNPGMF'

(50) Latin Name: *Punica granatum*
Varietal Denomination: SMNPGMF

(71) Applicant: Megan M Mathey, Holland, MI (US)

(72) Inventor: Megan M Mathey, Holland, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/350,936

(22) Filed: Jan. 31, 2019

(51) Int. Cl.
*A01H 5/02* (2018.01)
*A01H 6/00* (2018.01)

(52) U.S. Cl.
USPC ..... Plt./210

(58) Field of Classification Search
USPC ..... Plt./210
CPC ... A01H 5/08; A01H 5/00; A01H 5/02; A01H 6/00
See application file for complete search history.

*Primary Examiner* — June Hwu
(74) *Attorney, Agent, or Firm* — Cassandra Bright

(57) ABSTRACT

A new and distinct *Punica* cultivar named 'SMNPGMF' is disclosed, characterized by highly floriferous dwarf plants producing vibrant flowers and small fruits. Plants are heat and drought tolerant with excellent container performance. The new variety is a *Punica*, normally used for outdoor ornamental purposes.

2 Drawing Sheets

Latin name of the genus and species: *Punica granatum.* Variety denomination: 'SMNPGMF'.

BACKGROUND OF THE INVENTION

The new *Punica* cultivar is a product of a planned breeding program conducted by the inventor, Megan Mathey, in Grand Haven, Mich. The objective of the breeding program was to develop new pomegranate varieties with smaller plant forms and more flowers. The open pollination resulting in this new variety was made during July of 2015.

The seed parent is *Punica granatum* 'State Fair', unpatented. The pollen parent is unidentified. The new variety was selected in Summer of 2016 by the inventor in a group of seedlings resulting from the 2015 open pollination, in a nursery in Grand Haven, Mich.

Asexual reproduction of the new cultivar was performed by softwood cuttings. This was first performed at the same nursery in Grand Haven, Mich. in Summer of 2016, and has shown that the unique features of this cultivar are stable and reproduced true to type in multiple successive generations.

SUMMARY OF THE INVENTION

The cultivar 'SMNPGMF' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNPGMF' These characteristics in combination distinguish 'SMNPGMF' as a new and distinct *Punica* cultivar:

1. Good container plant.
2. Dwarf plant.
3. Vibrant flower color.
4. Very floriferous.
5. Heat and drought tolerant.

PARENT COMPARISON

Plants of the new cultivar 'SMNPGMF' are similar to plants of the seed parent in most horticultural characteristics; however, plants of the new cultivar 'SMNPGMF' differ in the following;

1. The new variety produces smaller fruit than the parent variety.
2. The new variety is an overall smaller plant than 'State Fair'.

COMMERCIAL COMPARISON

Plants of the new cultivar 'SMNPGMF' are comparable to the commercial variety *Punica* 'Sochi Dwarf', unpatented. The two *Punica* varieties are similar in most horticultural characteristics; however, the new variety 'SMNPGMF' differs in the following;

1. The new variety is more floriferous than this comparator.
2. New variety is a smaller plant than the comparator.
3. New variety produces smaller fruit than the comparator.

BRIEF DESCRIPTION OF THE PHOTOGRAPHS

Figure 1:
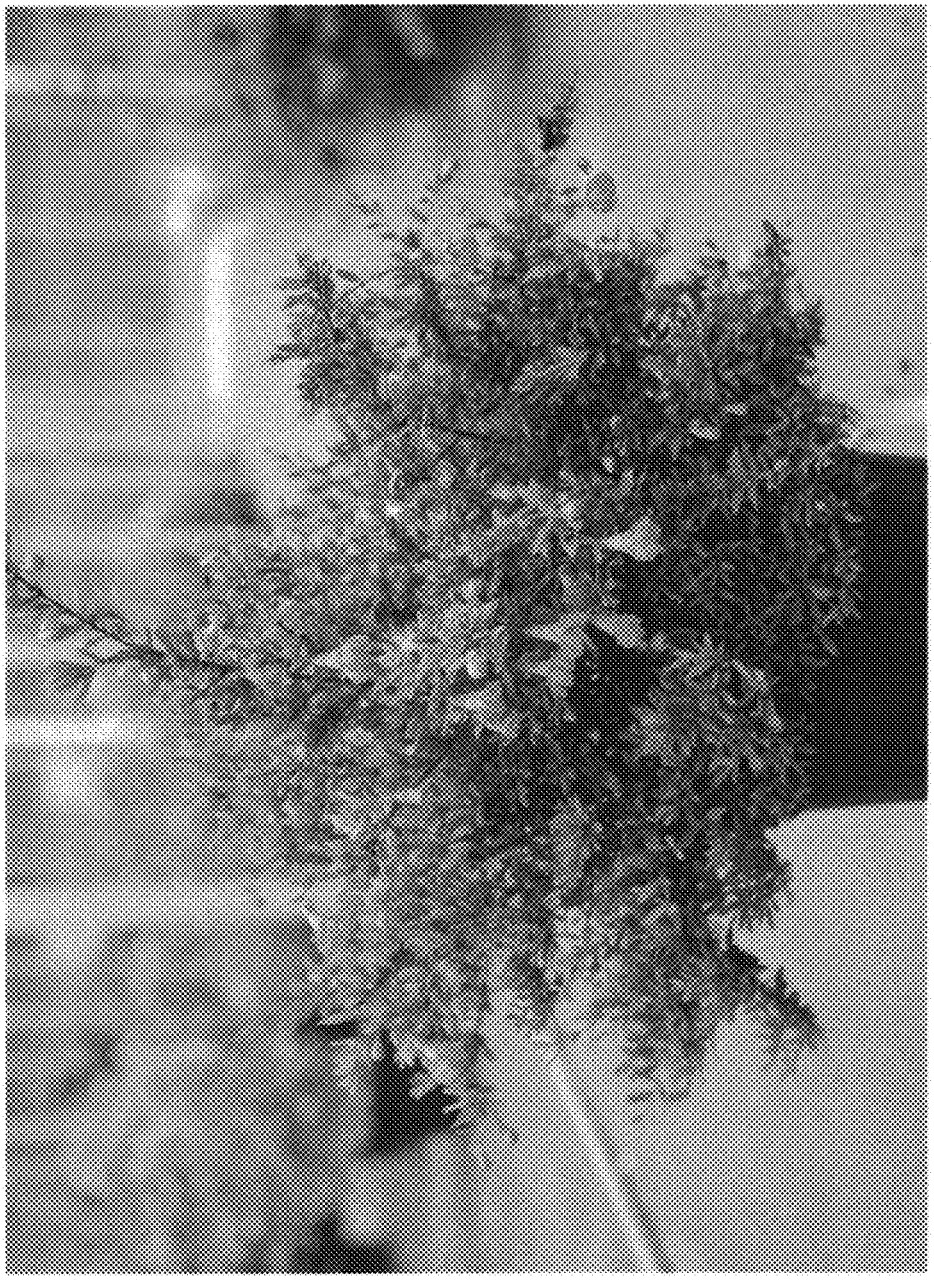

The accompanying photograph in FIG. 1 illustrates in full color a typical plant of 'SMNPGMF' in a 3 gallon pot. Age of the plant photographed is approximately 2-3 years old from a rooted cutting.

Figure 2:
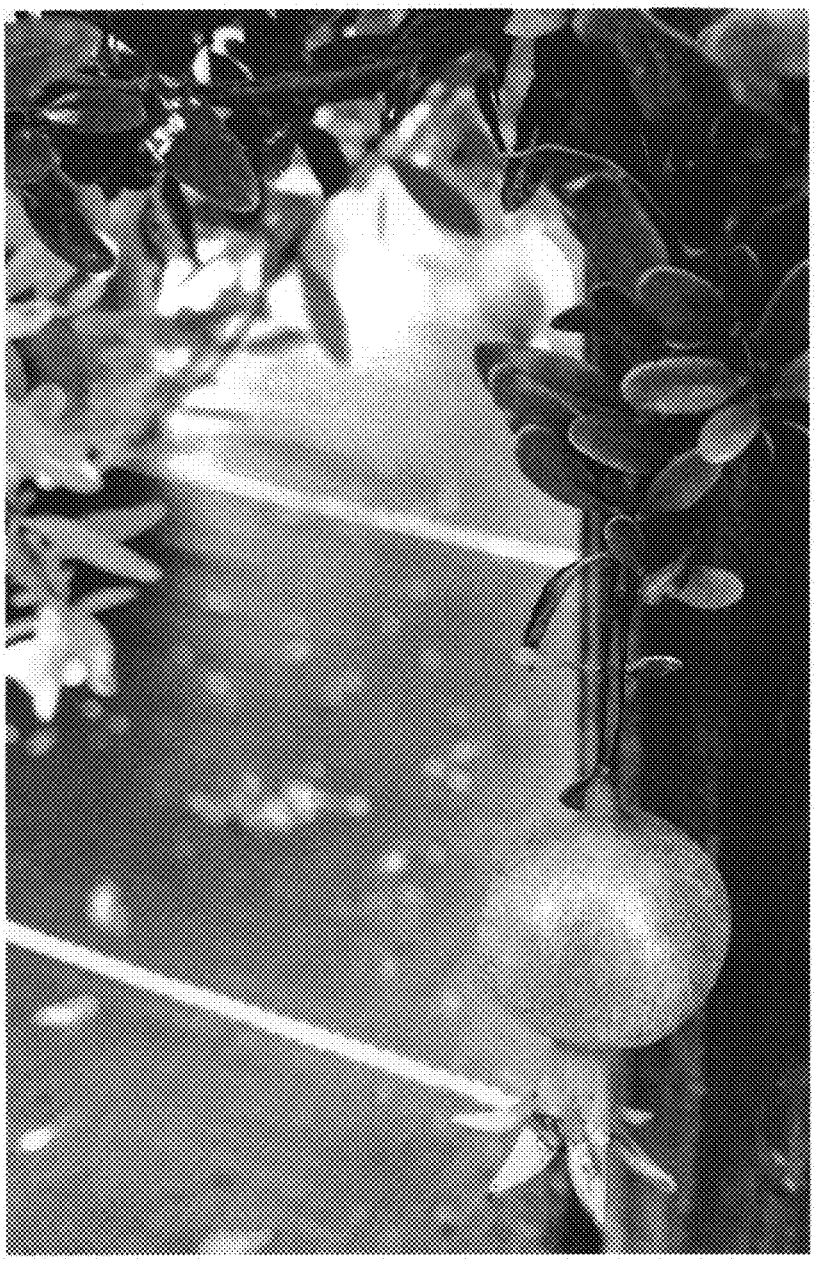

FIG. 2 illustrates a close up view of the fruit.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNPGMF' plants grown in a poly house during summer of 2018, in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Punica granatum* 'SMNPGMF'.

PROPAGATION

Type of propagation typically used: Softwood cuttings.
Time to initiate roots: 21 days at 18-27° C.
Time to produce a rooted cutting: 1-2 months at 18-27° C.
Root description: Thin, fibrous, moderately dense, freely branching. White to brown in color, not accurately measured with R.H.S. Chart.

PLANT

Age of plant described: 1-2 years old from a rooted cutting.
Container size: 3 gallon container.
Overall plant shape: Irregularly rounded.
Growth habit: Globular flowering shrub.
Plant spread: 73 cm.
Plant height: 62 cm.
Plant vigor: Moderately vigorous.
Branching habit: Free branching, upward and outward.
Length of primary lateral branches: 48 cm.
Diameter of lateral branches: 6 mm.
Quantity of lateral branches: 100.
Stem:
- *Color*.—RHS Brown 200D.
- *Shape*.—Round.
- *Strength*.—Strong.
- *Aspect angle*.—20 to 70 degrees from center.
- *Pubescence*.—None.

Thorns:
- *Length*.—About 1-2 cm.
- *Location*.—Lower branches.
- *Color*.—RHS Grey-Brown 199B.

Internode length: 1.0 cm.

FOLIAGE

Leaf:
- *Arrangement*.—Opposite, single.
- *Average length*.—1.5 cm.
- *Average width*.—7 mm.
- *Shape of blade*.—Oblong.
- *Apex*.—Obtuse.
- *Base*.—Obtuse.
- *Margin*.—Entire.
- *Texture of top surface*.—Smooth.
- *Texture of bottom surface*.—Smooth.
- *Color*.—Young foliage upper side: RHS Green 143A. Young foliage under side: RHS Yellow-Green 144A. Mature foliage upper side: RHS Green 143A. Mature foliage under side: RHS Yellow-Green 144A.
- *Venation*.—Type: Pinnate. Venation color upper side: RHS Yellow-Green 144D. Venation color under side: RHS Yellow-Green 144A.
- *Petiole*.—Length: 1 mm. Diameter: 0.5 mm. Texture, upper side: Slightly pubescent. Texture, under side: Slightly pubescent. Color, upper side: RHS Greyed-Red 180B. Color, under side: RHS Greyed-Red 180B.

FLOWER

Natural flowering season: June through July.
Inflorescence form: Single terminally occurring flowers.
Flowers per lateral stem: One flower at terminal end of branch.
Flowers and buds per plant: About 300 to 400.
Individual flowers:
- *Shape*.—Extended tubular campanulate.
- *Diameter*.—2 cm.
- *Length*.—4 cm.
- *Aspect*.—Pendulous.
- *Persistence*.—Self-cleaning.
- *Fragrance*.—None.

Petals:
- *Arrangement*.—Rotate, base fused into extended funnel.
- *Number*.—5 to 6.
- *Shape*.—Unfused, obovate.
- *Margin*.—Entire to slightly crenate.
- *Tip shape*.—Obtuse.
- *Base shape*.—Fused.
- *Length*.—2 cm.
- *Width*.—1.5 cm.
- *Texture*.—Upper: Smooth, moderately wrinkled. Lower: Smooth, moderately wrinkled.
- *Color*.—When opening: Upper surface: RHS Orange-Red 33A. Under surface: RHS Orange-Red 33A. Fully opened: Upper surface: RHS Orange-Red 33A. Under surface: RHS Orange-Red 33A.

Bud:
- *Shape*.—Dumbell.
- *Length*.—2.5 cm.
- *Diameter*.—1 cm.
- *Color*.—RHS Orange-Red N30C mixed with Orange-Red 32B.

Sepals:
- *Arrangement*.—Whorl.
- *Shape*.—Deltoid.
- *Tip shape*.—Acute.
- *Base shape*.—Fused.
- *Margin*.—Entire.
- *Quantity per flower*.—6.
- *Length*.—1 cm.
- *Width*.—4 mm.
- *Texture*.—Upper: Smooth, waxy. Lower: Smooth, waxy.
- *Color*.—Upper: RHS Orange-Red N30C mixed with Orange-Red 32B. Lower: RHS Red 41C.

Calyx:
- *Shape*.—Funnelform.
- *Length*.—2.5 cm.
- *Diameter*.—1 cm.

Peduncle:
- *Length*.—3 mm.
- *Diameter*.—2 mm.
- *Texture*.—Smooth, waxy.
- *Angle*.—45-90 degrees.
- *Color*.—RHS Orange-Red N30C mixed with Orange-Red 32B.
- *Strength*.—Good.

Pedicel: None.

REPRODUCTIVE ORGANS

Stamens:
*Number*.—About 100.
*Filament length*.—5 mm.
*Filament color*.—RHS Red 36B.
Anthers:
*Shape*.—Globular.
*Length*.—2 mm.
*Color*.—RHS Yellow-Orange 18A.
*Pollen*.—Amount: Moderate. Color: RHS Yellow-Orange 18A.
Pistil:
*Number*.—1.
*Length*.—1 cm.
*Style*.—Length: 2 cm. Color: RHS Green-Yellow 1D.
Stigma:
*Shape*.—Globular.
*Color*.—RHS Green-Yellow 1D.
*Ovary color*.—RHS Green-Yellow 1D.

OTHER CHARACTERISTICS

Fruits and seeds: One fruit produced per flower.
*Length*.—About 3-4 cm.
*Diameter*.—About 3-4 cm.
*Texture*.—Smooth.
*Color*.—RHS Greyed-Orange 170A lightly speckled Yellow 2B.
*Crown*.—
*Average height*.—When open 2 cm, closed 2.5 cm.
*Average diameter*.—When open 1.5 cm, closed 1.0 cm.
*Quantity of lobes*.—5-6.
*Position of lobes*.—Mainly upright, slight outward flare with maturity.
*Crown color*.—Near RHS Yellow-Green 154A.
*Aril shape*.—Obovate: teardrop shape with flattened/faceted sides.
*Aril color*.—Near RHS Red 46D, transparent, seed visible.
*Seed color*.—Near RHS White 155C.
*Seed size and shape*.—Irregular cylindric, with one end acute and one end truncate. Approximately 4 mm long and 2 mm wide One seed per aril.
Disease/pest resistance: Neither resistance nor susceptibility to normal diseases and pests of *Punica* observed.
Temperature range: Observed to tolerate a temperature range from −28° C. to 35° C. Root hardy to −28 C., top of the plant does die back to the ground.

What is claimed is:

1. A new and distinct cultivar of *Punica* plant named 'SMNPGMF' as herein illustrated and described.

* * * * *